(12) United States Patent
Hicks

(10) Patent No.: US 6,297,042 B1
(45) Date of Patent: Oct. 2, 2001

(54) CHEESE MAKING WITH BACTERIOPHAGE RESISTANT BACTERIA

(75) Inventor: Clair L. Hicks, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 08/440,734

(22) Filed: May 15, 1995

(51) Int. Cl.7 .................................................. C12N 1/12
(52) U.S. Cl. ..................... 435/252.1; 426/34; 426/36; 426/41; 426/42; 426/43; 435/236; 435/235.1; 435/252.9; 435/253.4
(58) Field of Search .................................. 426/34, 36, 41, 426/42, 43; 435/252.1, 252.9, 253.4, 260, 236, 235.1

(56) References Cited

U.S. PATENT DOCUMENTS

| | | | |
|---|---|---|---|
| 3,998,700 | * 12/1976 | Keinbold et al. ................. | 435/252.4 |
| 4,104,126 | * 8/1978 | Young ....................................... | 435/5 |
| 4,282,255 | * 8/1981 | Sandine et al. ........................... | 426/7 |
| 4,379,170 | 4/1983 | Hettinga et al. ........................ | 426/40 |
| 4,402,986 | 9/1983 | Sinkoff et al. ........................... | 426/41 |
| 4,544,637 | * 10/1985 | Keggins et al. .................. | 435/253.6 |
| 4,554,165 | 11/1985 | Richardson ............................ | 426/36 |
| 4,766,076 | * 8/1988 | Sandine et al. ................... | 435/253.6 |
| 4,847,096 | 7/1989 | Mellqvist et al. ...................... | 426/41 |
| 4,981,704 | 1/1991 | Thibault ................................. | 426/41 |
| 5,172,193 | * 12/1992 | Payne et al. ......................... | 356/442 |
| 5,338,682 | 8/1994 | Saski et al. ............................ | 426/42 |
| 5,360,617 | 11/1994 | Gasson .................................. | 426/36 |

OTHER PUBLICATIONS

Nordstrom et al. *J of Virology* 14(2) 1974, pp. 203–206.*

* cited by examiner

*Primary Examiner*—Leon B. Lankford, Jr.
(74) *Attorney, Agent, or Firm*—King and Schickli PLLC

(57) ABSTRACT

A method is provided for reducing or preventing bacteriophage attack on bacteria used in a cheese making process. The method includes (a) treating a blocker peptide precursor with a protease enzyme that hydrolyzes the precursor to produce blocker peptides; (b) collecting the blocker peptides so produced; (c) formulating a starter media with the blocker peptides; (d) growing bulk cultures of cheese making bacteria in the inoculated starter media; and (e) adding bacteria grown in the inoculated starter media to a fermentation medium for producing cheese. The present invention also includes a method of making cheese and cheese produced by the method.

17 Claims, 2 Drawing Sheets

CHEESE MAKING WITH BACTERIOPHAGE RESISTANT BACTERIA

TECHNICAL FIELD

The present invention relates generally to the art of cheese making and, more particularly, to a method of improving the productivity of the cheese making process and the quality of a cheese product by preventing bacteriophage attack on bacteria used in the cheese making process.

BACKGROUND OF THE INVENTION

Cheese is a milk product that is generally rich in flavor and contains many high-quality nutrients. There are a great many varieties of cheese but all are produced in a similar manner. First, raw or pasteurized milk is cultured, clotted by acid, rennet or both. The resulting curd is then cut and shaped into the desired form with or without pressing. Fresh cheeses such as cottage cheese or cream cheese do not require any further processing. Other varieties of cheese are, however, subsequently cured or ripened to obtain a desired consistency, flavor and aroma. These characteristics are produced by a partial breakdown of milk proteins and fat by the action of microbial, milk and rennet enzymes.

The acid produced during the manufacture of cheese results from the fermentation of the milk sugar, lactose. Generally, this fermentation is initiated by the addition to the milk of a culture of specially selected acid bacteria. Known as a starter culture, many different types of lactic acid bacteria may be utilized for this purpose. The acid production in the cheese curd resulting from the activity of the starter culture advantageously functions to retard the growth of other bacteria that would otherwise cause undesirable fermentations in the cheese. Further, the acid production also favors the expulsion of the whey and the fusion of the curd particles.

The lactic acid starter cultures utilized in cheese making may comprise single or mixed strains of bacteria. All, however, must convert milk sugar in the curd into lactic acid within a reasonable time if a high quality cheese is to result. Several factors may, however, prevent this conversion. Of these factors, the most important is bacteriophage attack. Specifically, cheese production loss due to phage attacks on lactic culture is the number one problem faced by the dairy products industry today.

Bacteriophages or phages, are viruses that attack a lactic acid bacteria cell, commandeer the biosynthetic or reproductive machinery of the cell, produce new phages and in the process lyse the bacteria cell. Phages are prevalent in cheese making facilities. They may contaminate the milk in a number of ways including through use of infected starter cultures or through contact with phage-carrying dust particles.

Phages effectively slow down or totally inhibit the activity of the starter culture. As a result, the milk fermentation medium is often insufficiently soured and insufficient acid is produced to retard the growth of undesirable bacteria that cause undesired fermentation products. Hence, the cheese spoils resulting in an undesired consistency, flavor, and/or aroma.

It is known that phage multiplication is influenced by temperature, pH and calcium content of the medium among other factors. While phage outbreaks can be at least partially controlled by rigorous hygienic handling of starters, by culture rotation and/or by culturing starters in calcium-reduced media, further improvements in controlling phage proliferation and attacks on starter cultures are desired. Toward this end, however, it should be appreciated that attempts to isolate phage-resistant strains have generally not met with success. A need is therefore identified for an improved method of controlling bacteriophage attacks on lactic acid bacteria utilized in the cheese making process.

SUMMARY OF THE INVENTION

Accordingly, it is a primary object of the present invention to provide an improved method of reducing or preventing bacteriophage attack on bacteria used in the cheese making process, overcoming the above-described limitations and disadvantages of the prior art.

An additional object of the present invention is to provide a simple and effective method of controlling bacteriophage attacks on lactic acid bacteria used in the cheese making process wherein the bacteria are protected against attack. Specifically, blocker peptides are produced and collected. These blocker peptides attach to sites on the cheese making bacteria and subsequently prevent attachment of bacteriophages so that the bacteria may continue to function normally, fermenting milk sugar and producing the desired curd more effectively and efficiently. As a direct consequence of the resulting faster processing time, if any bacteriophage infection does take place it is limited and localized and, therefore, does not have a substantial adverse effect on the resulting cheese product. Superior quality and greater productivity is therefore insured.

Still another object of the present invention is to provide a related method of making cheese with bacteriophage resistant cheese making bacteria as well as a relatively high quality cheese with more uniform consistency, flavor and aroma.

Additional objects, advantages and other novel features of the invention will be set forth in part in the description that follows and in part will become apparent to those skilled in the art upon examination of the following or may be learned with the practice of the invention. The objects and advantages of the invention may be realized and obtained by means of the instrumentalities and combinations particularly pointed out in the appended claims.

To achieve the foregoing and other objects, and in accordance with the purposes of the present invention as described herein, a method is provided for controlling (e.g. reducing or preventing) bacteriophage attack on bacteria such as lactic acid bacteria starter culture used in a cheese making process. The method includes the steps of treating a blocker peptide precursor selected from a group consisting of a source of immunoglobulins, bacteriophages, bacteriophage parts or mixtures thereof with a protease enzyme that hydrolyzes the blocker peptide precursor. The method also includes the collecting of the blocker peptides produced by the hydrolysis of the blocker peptide precursor and the formulating and heat treating of a starter media with the blocker peptides. Finally, the method includes the additional steps of growing bulk cultures of bacteria used in the cheese making process in a peptide containing starter media and adding the bacteria grown in the peptide containing starter media to a fermentation medium for producing cheese.

More specifically describing the invention, the source for immunoglobulins may include raw whey, dried whey, whey protein isolates, non-fat dried milk, blood serum protein isolates, purified immune protein preparations and mixtures thereof. Preferably, the bacteriophage parts includes spikes, tail fibers, filaments and mixtures thereof. Also, the enzyme used in the present method is preferably selected from a group consisting of papain, bromelain, ficin and mixtures thereof. Of these, papain appears to be the most preferred enzyme.

In accordance with a further aspect of the present invention, a method of making cheese with bacteriophage resistant cheese making bacteria is provided. In addition to the above steps, this method includes the cutting of the curd. Specifically, the curd is cut at a selected time in an effort to increase cheese yield and maximize the result and quality of the cheese. For example, the curd may be cut in accordance with the method set forth in my co-pending U.S. Pat. No. 5,172,193 entitled "Method of Predicting Cut-Time of Milk Coagulum in Cheese-Making Process". Further, the method may include the additional step of curing the curd to provide a cheese of desired consistency, flavor and aroma. Any known method of curing may be utilized to produce a cheese of desired qualities. Cheeses produced in accordance with the present method are also the subject of the present invention.

Still other objects of the present invention will become apparent to those skilled in this art from the following description wherein there is shown and described a preferred embodiment of this invention, simply by way of illustration of one of the modes best suited to carry out the invention. As it will be realized, the invention is capable of other different embodiments and its several details are capable of modification in various, obvious aspects all without departing from the invention. Accordingly, the drawings and descriptions will be regarded as illustrative in nature and not as restrictive.

BRIEF DESCRIPTION OF THE DRAWING

The accompanying drawing incorporated in and forming a part of the specification, illustrates several aspects of the present invention and together with the description serves to explain the principles of the invention. In the drawing.

Figure 1:
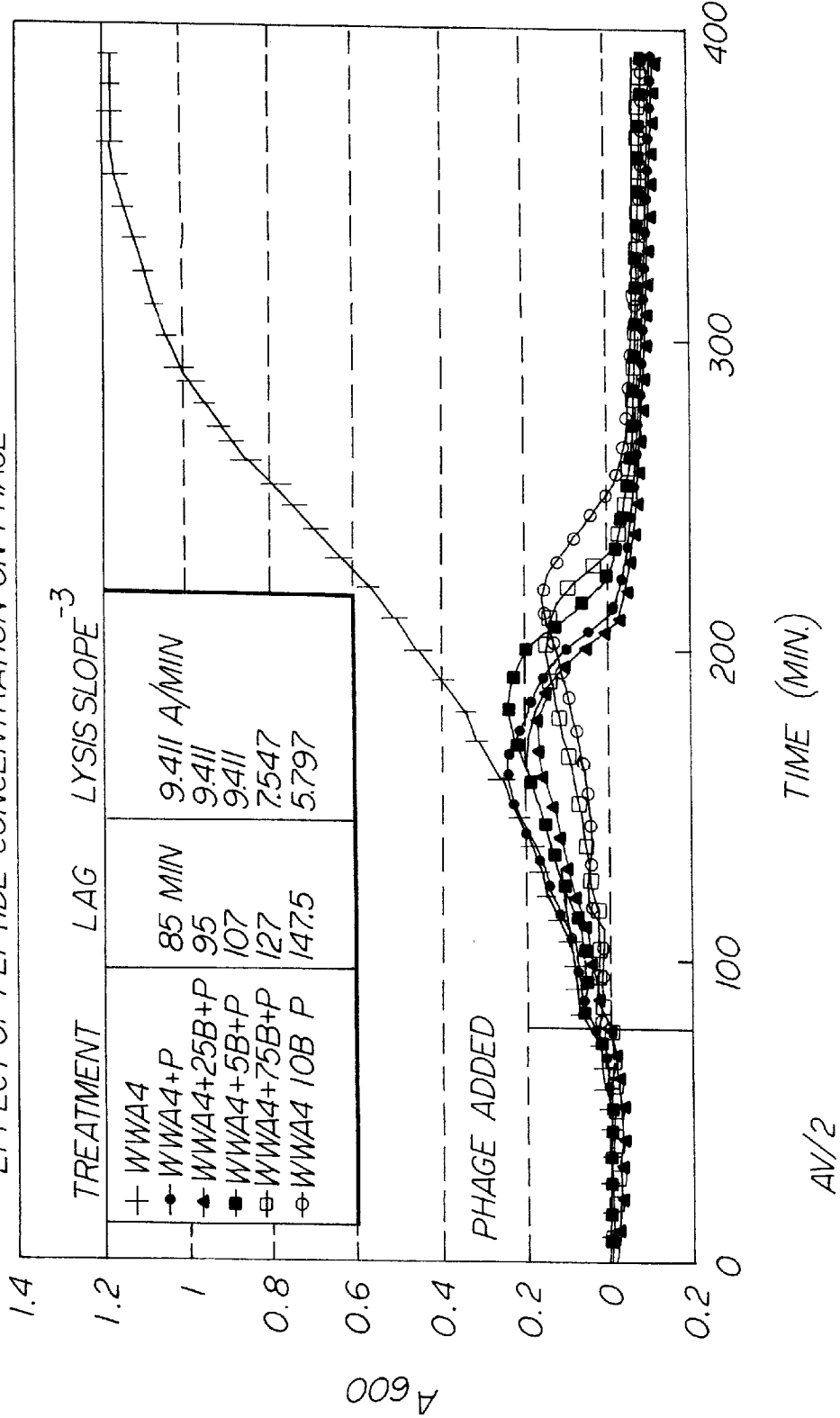
FIG. 1 is a graphical representation comparing lactic acid bacteria starter culture as a control with starter culture inoculated in accordance with the teachings of the present invention in various concentrations followed by phage introduction at various concentrations.

Reference will now be made in detail to the present preferred embodiment of the invention, an example of which is illustrated in the accompanying drawing.

DETAILED DESCRIPTION OF THE INVENTION

A method of controlling bacteriophage attack on bacteria used in a cheese making process will now be described in detail. The method includes the initial step of treating a blocker peptide precursor selected from a group consisting of a source of immunoglobulins, bacteriophages, bacteriophage parts and mixtures thereof with a protease enzyme that hydrolyses the blocker peptide precursor. Preferably, the source of immunoglobulins includes raw whey, dried whey, whey protein isolates, non-fat dried milk, blood serum protein isolates, purified immune protein preparations and mixtures thereof. It should be appreciated, however, that this list is presented only for purposes of illustration and the invention should not be considered as limited thereto.

The bacteriophage parts are preferably spikes, tail fibers, filaments and mixtures thereof. Still more specifically, the bacteriophages and parts thereof utilized as blocker peptide precursors are of a type or strain to which cheese making bacteria are sensitive. Generally, such cheese making bacteria include lactic acid bacteria such as available, for example, from CHR. Hansen's of Mississauga, Ontario including but not limited to mesophilic homofermentative, thermophilic and mesophilic aromatic cultures as marketed under the trademarks PHAGE CONTROL, DVS, PHAGE HARDENED, REDI-SET, SCO, ST/LH/LB, HR/HC, ITALIANO, CH-N, PS, DSG, CAF and FLORA DANICA. Of course, lactic acid starter cultures are available from other sources including, for example, Rhone-Poulenc (e.g. various Lactococcus, *lactis* ssp., *Lactococcus lactic* ssp. *cremoris*, and *Streptococcus thermophilous* cultures identified by culture numbers: D11-LF, D15, D30-LF, D37, D40-LF, D50, D52-LF, D62, D71, D75, D84, D107, D115, D120, D175, D180-LF, D205, D210, D220, D230, D250, D265, D270, D275, D509-LF, L12, M30, M32, M46, M49, M56, M58, M59, EZ 10, EZ 15, EZ 20, EZ 25, LF2, LF3, DPL 569, DPL 571, DPL 572, DPL 573, DPL 574, DPL 575, DPL 576, DPL 577, DPL 578, DPL 579, MA011, MA014, MA016, MA019, EZ100, EZ200, EZ300; various thermophilic cultures including *Streptococcus thermophilous, Lactobacillus delbruekeii* ssp. *bulaaricus, Lactobacillus helveticus* and *Lactobacillus delbruekeii* ssp. *lactis* cultures with the following culture numbers: C90, C100, C110, C120, C130, C150, C160, C180, C260, C280, C300, C310, C320, C330, C340, R110, R130, R150, R160, RX160, R170, R180, R190, TC120, TC234, TC246, TC257, TR160, TEX 1, TEX 2, TEX 3, CR5, CR12, CR14, LBST, KCR5, TA052, TA054, TA060, TA061, TA062, LH100, LB120; as well as additional mixed and pure cultures including the above species alone or in combination with *Lactococcus lactis* ssp. *lactis biovar diacetylactis, Leuconostoc mesenteroides* ssp. *cremoris, Bifidobacterium, Lactobacillus acidophilus, Lactococcus lactis* ssp. *lactis, Lactobacillus casei,* Propionibacterium, Freudenrecheii ssp. *shermanii, Bifidobacterium infantis, Bifidobacterium longum* including culture numbers: 801–805, 811–815, 831–835, 851–855, 901–905, 911–915, 921–925, 951–953, 201–205, VT3, OS, LD, FCS24, FLD, FMQ3, FOS, FRI, FVT3, Y604, Y605, Y610, Y611, Y612, Y613, Y617, Y650, Y651, Y653, ABY-2C, THY35, THY42, THY95, CAF, JVI, BC1, BC2, MD series, MM series, LC-20, FB302, FB304, PS31, TC120, TC234, LC, NCFM, NCFM, BBI, 403 AC, 410 BBI, 411 BBL. The enzyme utilized to hydrolyze the blocker peptide precursor may be selected from a group of protease enzymes including, for example, papain, bromelain, ficin and mixtures thereof. Preferably, papain is utilized. Papain cleaves the immunoglobulin IgG and IgM blocker peptide precursors at a most advantageous location to provide phage blocking activity. For best results, the concentration of blocker peptide precursor to enzyme should be maintained between 0.2–50.0 grams per 100 lbs of precursor (at a concentration of approximately 5% solids) and more preferably should be maintained at about 1 gram per 100 lbs of precursor (at a concentration of approximately 5% solids).

More particularly, the production of the blocker peptides may be completed in accordance with ultrafiltering and diafiltering techniques. Preferably, the blocker peptide precursor being treated with the enzyme is ultrafiltered through a polysulfone membrane cellulose or other membrane having a molecular weight cut-off of less than 20,000 Daltons. The permeate, that is, the material passing through the membrane, comprises peptides having a molecular weight of less than 10,000–20,000 Daltons, depending on the size of the membrane utilized in filtering.

As the blocker peptide permeate is collected, an appropriate dilutant (e.g. water, whey or pasteurized skim milk) may be added to the source of immunoglobulins treated with the enzyme. This is done volume-for-volume so that the original volume of the blocker peptide precursor and enzyme (i.e., the retentate) is substantially maintained at a given level. This serves to maintain substrate concentrations and reduce product inhibition. The enzymatic treatment of the blocker peptide precursor is completed at any appropriate temperature where enzymatic inactivation does not occur. However, temperatures just below the enzyme's point of denaturation are most efficient. Accordingly, for papain, the enzymatic treatment is completed between 30–50° C. and most preferably at approximately 40° C. Further, the enzymatic treatment is completed for a relatively extended period of time of at least two hours. This allows the enzyme to hydrolyze significant portions of the blocker peptide precursor. Of course, a greater concentration of enzyme may be used to shorten the processing time.

After collecting the blocker peptides produced by the hydrolysis of the blocker peptide precursor, the blocker peptides may be concentrated if desired utilizing, for example, reverse osmosis or evaporation in accordance with procedures well known in the art. These peptides may then be dried by using freeze drying, spray drying, or vacuum drying techniques also well known to those in the art. These dried blocker peptides may then be subsequently formulated into useable preparations or lactic growth media by, for example, mixing with appropriate carriers such as phosphate, citrate, buffers or water and growth stimulants such as yeast extract.

Next is the step of inoculating a growth or starter media with the blocker peptides. Such starter media for cheese making bacteria are well known in the art. Preferably, the starter media is formulated with blocker peptides having a concentration of about 5.0% dry weight when using a starter media in powered form. The starter media and peptide blocker premix is then mixed with distilled water. For best effect, the concentration of blocker in the growth or starter media after mixing with distilled water should at least be 0.5 mg/ml.

Lactic starter media containing blocker peptides are then heat treated using traditional methods known by those skilled in the art at temperatures such as 85° C. for 45 minutes, to destroy any microorganisms that may have contaminated the starter media. The starter media is then cooled for temperatures that supports the lactic culture of choice.

Next is the growing of bulk cultures of bacteria used in the cheese making process in this inoculated starter media. This is followed by adding the bacteria grown in the inoculated starter media to a fermentation media (e.g. raw or pasteurized milk) for producing cheese.

Advantageously, the blocker peptides bind and block binding sites/determinates on the bacteria thereby providing a competitive inhibition to subsequent phage attack. Accordingly, the cheese making bacteria continue to function normally fermenting the milk sugar and producing the desired curd more effectively and efficiently. In fact, fermentation processing time may be significantly reduced and, accordingly, (while unlikely) if any bacteriophage infection does take place it is limited and localized. Thus, such a bacteriophage infection does not have any substantial adverse effect on the quality of the resulting cheese product.

Accordingly, it should be appreciated that the present invention both increases productivity while also ensuring a more uniform and higher quality end product.

In accordance with still another aspect of the present invention, a method of making cheese with bacteriophage resistant cheese making bacteria further includes a step of cutting the resulting curd that is formed in the fermentation media by the activity of the cheese making bacteria. The cutting of the curd may be accomplished in accordance with any appropriate means known in the art at a time that may, for example, be identified by utilizing any of the methods set forth in my co-pending U.S. Pat. No. 5,172,193.

Further, the cheese making method may also include the step of curing the curd to provide a cheese of desired consistency, flavor and aroma. As is known in the art, curing consists of a series of biological and chemical changes that are affected by the moisture content, acidity, texture, shape, size, and microorganisms in the cheese. The chemical changes may include the breakdown of fats to fatty acids, proteins to amino acids, and lactose to various products including lactic, acidic and propionic acids, diacetyl, as well as carbon dioxide. Some of the flavorful products of the curing process include various volatile fatty acids, alcohols, esters, ketones, peptides, and amino acids produced during this process.

Figure 2:
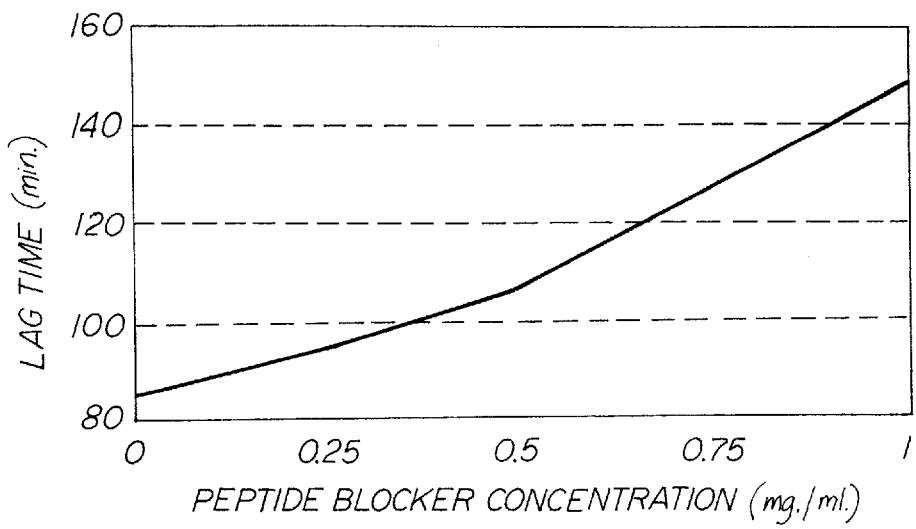
FIG. 2 is a graphical representation of the effect of peptide blocker concentration on the lag time before cell lyses begins following introduction of bacteriophage.
Figure 3:
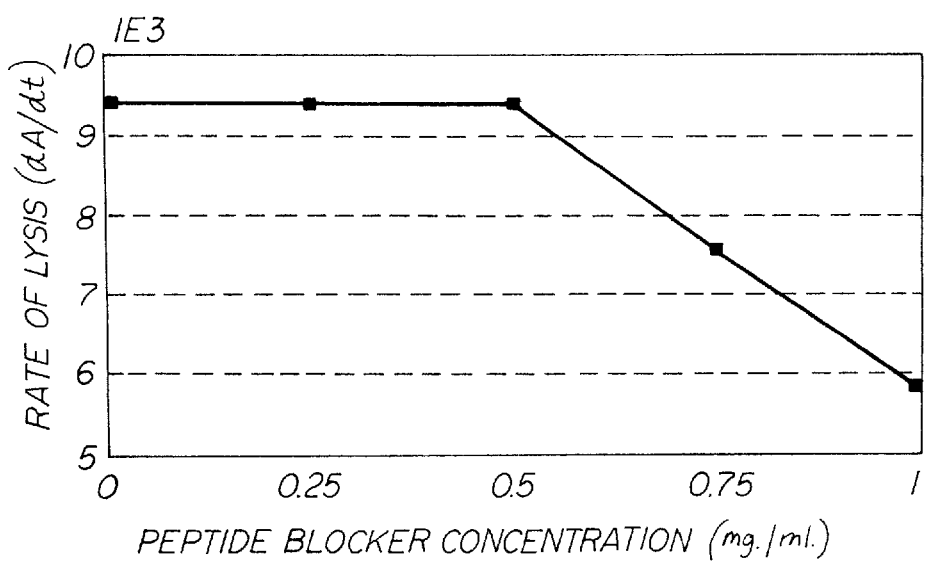
FIG. 3 is a graphical representation of the effect of peptide blocker concentration on the rate of lysing of lactic acid bacteria cells.

The advantageous effect of the method of the present invention produced by the peptide blockers on phage proliferation in a lactic acid bacteria culture is best demonstrated with reference to FIGS. 1–3. The phage concentration at the point of inoculation was $8.4 \times 10^5$/ml. Peptide blocker concentration includes approximately 72% lactose. As clearly demonstrated in FIG. 1, peptide blockers can inhibit phage attachment to lactic cells (*Lactococcus lactis* ssp. *lactis* WWA4). FIG. 2 graphically demonstrates the resulting increase in lag times (that is, the time from phage addition to point where rate of lysis exceeds cultured growth). FIG. 3 graphically demonstrates the resulting decrease in the lysis rate. Together, this data clearly suggests that the antigenic binding sites on the surface of the lactic bacteria cells are not competitively bound until a concentration of 0.5 mg/ml of blocker is added to the growth media. At blocker concentrations greater than 0.5 mg/ml, a competitive inhibition is observed between the phage and the blockers for the antigenic sites. Advantageously, when utilizing the blocker peptides in the present method, cheese vat phage proliferation is inhibited sufficiently so that the curd may be completely coagulated for cutting before phage attack becomes a significant problem adversely effecting quality of the cheese product.

The following examples are presented to further illustrate the invention, but are not to be considered as limited thereto.

EXAMPLE 1

Blocker peptides were prepared from a rennet whey blocker peptide precursor. Specifically, 5000 ml of rennet whey were treated with 500 mg of crude papain (Sigma Chemical Co., St. Louis, Mo.) while being ultrafiltered and diafiltered using a hollow fiber membrane (Supelco, Bellefonte, Pa.) with a molecular weight cut-off of 10,000 Daltons. The process ran for two hours at 40° C. The permeate was collected and freeze dried air dried for subsequent use as blocker peptides in controlling bacteriophage attack on bacteria in accordance with the present method.

EXAMPLE 2

Blocker peptides are prepared from a rennet whey blocker peptide precursor. Specifically, 5000 ml of rennet whey is treated with 500 mg of bromelain (ICN Biomedicals, Inc., Iruine, Calif.) while being ultrafiltered and diafiltered using a hollow fiber membrane (Supelco, Bellefonte, Pa.) with a molecular weight cut-off of 10,000 Daltons. The process runs for two hours at 40° C. The permeate is collected and freeze dried or air dried for subsequent use as blocker peptides in controlling bacteriophage attack on bacteria in accordance with the present method.

EXAMPLE 3

Blocker peptides are prepared from a rennet whey blocker peptide precursor. Specifically, 5000 ml of rennet whey is treated with 100 mg of ficin (ICN Biomedicals, Inc., Irvine, Calif.) while being ultrafiltered and diafiltered using a hollow fiber membrane (Supelco, Bellefonte, Pa.) with a molecular weight cut-off of 10,000 Daltons. The process runs for two hours at 40° C. The permeate is collected and freeze dried or air dried for subsequent use as blocker peptides in controlling bacteriophage attack on bacteria in accordance with the present method.

EXAMPLE 4

Lactic bacteria (*Lactococcus lactis* ssp. *lactis* WWA4, $1\times10^9$ cfu/ml) is added to growth or starter media M17. After 90 minutes, bacteriophage c2 ($2\times10^7$ pfu/ml) (i.e. a phage specific to the lactic bacteria grown in the starter media) is added to the culture. After approximately 120–150 minutes, the phage lyse all bacteria cells. The medium containing the phage is then disrupted using a tissue homogenizer, blender, sonicator or other disruptive device. The disrupted suspension of phage parts including spikes, tail fibers and filaments is then hydrolyzed with one or more protease enzymes such as papain, bromelain or ficin. Enzymatic hydrolysis takes place while the suspension is being ultrafiltered and diafiltered using a hollow fiber membrane with a molecular weight cut-off of, for example, 10,000 Daltons. The process runs for 2 hours at approximately 40° C. The permeate is collected and may be freeze dried air dried by any appropriate method known in the art. The permeate may then be subsequently utilized in the method of the present invention to control bacteriophage attack on bacteria used in the cheese making process.

EXAMPLE 5

*Lactococcus lactis* ssp. *lactis* C2 bulk starter (incubated at 26° C. for 16 hours in M17 broth) was used to inoculate (2%) media consisting of M17 broth with $CaCl_2$ (3 samples) and M17 broth with $CaCl_2$ plus fractionated whey peptide blocker (4%) (2 samples). Phage c2 ($2\times10^7$ pfu/ml) was added (1%) to four incubating cultures (26 C) (two with blocker, two without) at 30 min or 60 min after culture inoculation. Cell growth was observed ($A_{600nm}$) immediately after culture inoculation and at 20 min intervals for 5 hours. Blocker-containing media inhibited bacteriophage proliferation and decreased rate of cell lysis. Media with blocker extended cell growth time by 29.8 and 21.5 min for cultures inoculated with bacteriophage at 30 and 60 min, respectively. Rate of lysis generally increased with cell numbers. However, 55% and 52.5% reductions in rate of cell lysis were observed when cells were grown in blocker-containing media inoculated with bacteriophage at 30 and 60 min, respectively.

EXAMPLE 6

Peptides, fractionated from hydrolyzed whey, and collected through a 10,000 molecular weight cut off hollow fiber Romicon ultrafiltration membrane, were used to prepare a phage inhibitory medium. Bulk starter was prepared from M17 broth inoculated (4%) with WWA-SCO166-4 single strain lactic culture. M17 broth (heat treated at 85 C for 45 min and cooled to 24 C) containing whey peptide blockers (0, 0.025, 0.05, 0.075, and 0.1 g/mL) was inoculated with WWA-SCO 166-4 bulk starter and incubated for 6.0 hours. WWA4-phage were added to the growing culture ($10^3$ pfu/mL) after 90 min of incubation. Cell growth was monitored spectrometrically ($A_{600mm}$) at 10 min intervals. As peptide blocker concentration increased the time to bacterial cell lysis increased and the rate of bacterial lysis decreased. Time from phage introduction to maximum absorbance increased linearly from 85 min (o g/ml blocker) to 147.5 min (0.1 g/mL blocker). Slope of bacterial lysis did not change until blocker concentration exceeded 0.05 g/ml. A linear decrease in lysis rate was observed for blocker concentrations of 0.05 to 0.1 g/mL, suggesting that antigenic sites on the surface of lactic cells must be saturated before the attachment of phage could be competitively inhibited. In other experiments where phage concentration varied from $10^1$ to $10^3$ pfu/mL, time to maximum absorbance decreased as phage concentration increased. However, the time differential between media with and without blockers increased linearly with phage concentration suggesting that blocker concentration was most effective when lactic cell numbers were lowest.

What is claimed is:

1. A method of controlling bacteriophage attack on cheese making bacteria used in a cheese making process, comprising:

treating a blocker peptide precursor selected from a group consisting of a source of immunoglobulins, bacteriophages to which cheese making bacteria are sensitive, bacteriophage parts to which cheese making bacteria are sensitive and mixtures thereof with a protease enzyme that hydrolyzes the blocker peptide precursor;

collecting blocker peptides produced by hydrolysis of the blocker peptide precursor;

formulating a starter mediate with the blocker peptides and heat treating the formulated starter media;

growing bulk cultures of cheese making bacteria used in the cheese making process in the formulated starter media; and adding cheese making bacteria grown in the formulated starter media to a fermentation medium for producing cheese.

2. The method set forth in claim 1, wherein said source of immunoglobulins includes raw whey, dried whey, whey protein isolates, non-fat dried milk, blood serum protein isolates, purified immune protein preparations and mixtures thereof.

3. The method set forth in claim 1, wherein said bacteriophage parts include spikes, tail fibers, filaments and mixtures thereof.

4. The method set forth in claim 1, wherein said bacteriophage parts include spikes, tail fibers, filaments and mixtures thereof.

5. The method set forth in claim 1, wherein said enzyme is selected from a group consisting of papain, bromelain, ficin and mixtures thereof.

6. The method set forth in claim 2, wherein said enzyme is selected from a group consisting of papain, bromelain, ficin and mixtures thereof.

7. The method set forth in claim 3, wherein said enzyme is selected from a group consisting of papain, bromelain, ficin and mixtures thereof.

8. The method set forth in claim 4, wherein said enzyme is selected from a group consisting of papain, bromelain, ficin and mixtures thereof.

9. A method of making cheese with bacteriophage resistant cheese making bacteria, comprising:

formulating a starter media with peptides that block bacteriophage attachment sites on the cheese making bacteria;

growing bulk cultures of the cheese making bacteria in the formulated starter media;

adding the cheese making bacteria grown in the formulated starter media to a fermentation media for producing cheese whereby a curd is formed; and cutting the curd.

10. The method set forth in claim 9, including a further step of curing the curd to provide a cheese of desired consistency, flavor and aroma.

11. The method set forth in claim 10, further including:

treating a blocker peptide precursor selected from a group consisting of a source of immunoglobulins, bacteriophages, bacteriophage parts and mixtures thereof with a protease enzyme that hydrolyzes the blocker peptide precursor; and collecting blocker peptides produced by hydrolysis of the blocker peptide precursor, said collected blocker peptides being utilized to inoculate the starter media.

12. The method set forth in claim 11, wherein said source of immunoglobulins include raw whey, dried whey, whey protein isolates, non-fat dried milk, blood serum protein isolates, purified immune protein preparations and mixtures thereof.

13. The method set forth in claim 12, wherein said bacteriophage parts include spikes, tail fibers, filaments and mixtures thereof.

14. The method set forth in claim 10, wherein said bacteriophage parts include spikes, tail fibers, filaments and mixtures thereof.

15. The method set forth in claim 10, wherein said enzyme is selected from a group consisting of papain, bromelain, ficin and mixtures thereof.

16. The method set forth in claim 12, wherein said enzyme is selected from a group consisting of papain, bromelain, ficin and mixtures thereof.

17. The method set forth in claim 14, wherein said enzyme is selected from a group consisting of papain, bromelain, ficin and mixtures thereof.

* * * * *